United States Patent [19]

Stanbro et al.

[11] Patent Number: 4,728,882

[45] Date of Patent: Mar. 1, 1988

[54] CAPACITIVE CHEMICAL SENSOR FOR DETECTING CERTAIN ANALYTES, INCLUDING HYDROCARBONS IN A LIQUID MEDIUM

[75] Inventors: William D. Stanbro, Columbia; Arnold L. Newman, Kensington, both of Md.

[73] Assignee: The Johns Hopkins University, Baltimore, Md.

[21] Appl. No.: 846,778

[22] Filed: Apr. 1, 1986

[51] Int. Cl.⁴ .............................. G01R 27/26
[52] U.S. Cl. ...................... 324/61 R; 324/61 P; 324/71.5; 204/1 T; 204/400
[58] Field of Search ............ 324/61 R, 61 P, 71.5; 204/1 T, 400

[56] References Cited

U.S. PATENT DOCUMENTS

| | | | |
|---|---|---|---|
| 3,350,941 | 11/1967 | Misevich et al. | 73/336.5 |
| 3,874,223 | 4/1975 | Miyazaki et al. | 340/623 X |
| 4,057,823 | 11/1977 | Burkhardt et al. | 357/52 |
| 4,184,952 | 1/1980 | Stewart | 210/781 |
| 4,203,087 | 5/1980 | Kovac et al. | 338/35 |
| 4,214,203 | 7/1980 | Coster et al. | 324/425 |
| 4,240,028 | 12/1980 | Davis, Jr. | 324/61 R |
| 4,247,299 | 1/1981 | Klein et al. | 324/61 R |
| 4,264,331 | 4/1981 | Klein et al. | 436/151 |
| 4,335,379 | 6/1982 | Martin | 324/451 X |
| 4,411,741 | 10/1983 | Janata | 324/71.5 X |
| 4,423,371 | 12/1983 | Senturia et al. | 324/61 R |
| 4,453,126 | 6/1984 | Volgyesi | 324/61 R |
| 4,517,547 | 5/1985 | Gray et al. | 340/59 |
| 4,571,543 | 2/1986 | Raymond et al. | 324/61 R X |

FOREIGN PATENT DOCUMENTS 2137361 10/1984 United Kingdom .

Primary Examiner—Reinhard J. Eisenzopf
Assistant Examiner—Robert W. Mueller
Attorney, Agent, or Firm—Robert E. Archibald; Howard W. Califano

[57] ABSTRACT

An apparatus for detecting the concentration of certain analytes, including hydrocarbons, in a liquid medium, is disclosed. The apparatus uses a planar or "open" capacitor containing an active layer. In response to selected analyte in the liquid medium, the active layer causes capacitance to decrease with increasing analyte concentration. The capacitance decreases because higher dielectric water molecules are displaced from a region of the capacitor's electric field. For certain hydrocarbon analytes having high Henry's Law constants, the active layer causes bubbles to nucleate in the liquid medium on the surface of the active layer. Bubble formation displaces water molecules and decreases capacitance.

45 Claims, 9 Drawing Figures

CAPACITIVE CHEMICAL SENSOR FOR DETECTING CERTAIN ANALYTES, INCLUDING HYDROCARBONS IN A LIQUID MEDIUM

STATEMENT OF GOVERNMENTAL INTEREST

The Government has rights in this invention pursuant to Contract No. N00024-85-C-5301, awarded by the Department of the Navy.

BACKGROUND OF THE INVENTION

1. Field of the Invention

The present invention relates to a capacitive sensor that may be used to detect small traces of hydrocarbon molecules, and other selected analytes, in liquid medium. The uses of the invented sensor would include, but are not limited to: detecting trace hydrocarbon pollutants in ground water or streams; oil exploration; and, detecting trace substances in industrial and laboratory processes.

2. Description of the Prior Art

It has been the desire of engineers and scientists in the environmental, geological, and chemical process fields to have a reliable sensor to detect traces of hydrocarbon molecules in solutions. In the environmental field, such a sensor would detect hydrocarbon pollutants in ground water and streams, originating from industrial sites or storage tanks. In the geological field, such a sensor would be used to detect trace hydrocarbons in ground waters or at off shore sites to locate potential oil exploration areas. In the chemical process field, such a sensor would detect trace substances in industrial and laboratory processes. However, the prior art did not provide a sensitive and reliable sensor to detect such low concentrations of hydrocarbon analytes in solution.

Various prior art references teach detecting traces of water in pipes carrying oil. In U.S. Pat. No. 4,240,028 issued to Davis, Jr., and U.S. Pat. No. 4,517,547 issued to Gray et al, traces of water in oil are detected as the fuel mixture passes in a pipe through a capacitive sensor. The bulk dielectric of the oil in the pipe is increased by traces of water molecules. In U.S. Pat. No. 4,184,952 issued to Steward, a similar technique is used to measure basic sediment and water (BS&W) in crude oil. However, the above sensors do not have the sensitivity to detect low concentrations of hydrocarbons.

Various capacitive sensors are taught in the art to detect humidity in the air or anesthetic gas in a gas mixture delivered to a patient during various medical procedures. U.S. Pat. No. 3,350,941 issued to K. W. Misevich et al and U.S. Pat. Nos. 4,203,087 and 4,277,742 issued to Kovac et al, disclose capacitive humidity sensors. These humidity sensors use a moisture sensitive layer which absorbs water vapor. The dielectric property of the layer changes as it is penetrated by water vapors. As the moisture content of the air increases the capacitance of the humidity sensor increases.

U.S Pat. No. 4,453,126 issued to G. A. Volgyesi and a published U.K. patent application GB No. 2 137 361 A, teach an apparatus for measuring anesthetic gas in a breathing mixture supplied to a patient. For both references, a planar capacitor is coated with a polymeric or lipid layer. The physical or chemical properties of the polymeric or lipd layer change with increasing concentration of the anesthetic gas, causing a change in the dielectric constant of the layer. These references report that an increase in the concentration of the anesthetic gas causes an increase in the capacitance of the sensor. The prior art anesthetic gas sensors use a reference sensor to compensate for the humidity of the gas mixture.

SUMMARY OF THE INVENTION

The present invention is a new sensor for determining the presence of trace analytes, such as hydrocarbons, in a liquid medium. In one embodiment, the invention uses a unique mechanism that produces nucleated bubbles in the liquid medium adjacent to the surface of a concentrating layer. The formation of such nucleated bubbles in the liquid layer adjacent to the concentrating layer lowers the measured capcitance of the sensor. This mechanism provides high sensitivity to trace hydrocarbon or other selected analytes in solution.

The invention utilizes an "open" or planar capacitor which comprises: a first and second conductor or electrode positioned on a substrate and disposed a distance from each other to form a channel; a first electrically insulating layer that covers the conductors; and, an active or concentrating layer, that has a high affinity for non-polar molecules, which then coats the two insulated conductors and may fill a portion of the channel formed between the electrodes. When an alternating voltage is applied across the conductors, an electric field is generated having lines of flux that cross the channel and bridge the volume between the conductors.

In operation, the surface of the "open" capacitor is exposed to a liquid medium containing hydrocarbons, or other selected analyte molecules. When the capacitive sensor is exposed to such a liquid medium, the capacitance of the sensor decreases as the concentration of the analyte increases. Applicants have observed two different classes of response from hydrocarbon analytes in an aqueous solution.

The first observed class produces a rapid decrease in capacitance as the concentration of certain acyclic hydrocarbons increases. A unique bubble generating mechanism accounts for the extreme sensitivity of the sensor. It has been found that bubbles nucleate in the liquid medium on the surface of the concentrating layer in proportion to the concentration of the analyte. The nucleated bubbles, which have a dielectric constant of 1-3, form on the interface between the liquid medium and the concentrating layer. Formation of these bubbles displaces water molecules, which have a dielectric constant approximately equal to or greater than 78, from the sensor's electric field. This modification to the dielectric properties of the environmental liquid layer adjacent to the sensor causes a significant decrease in the capacitance of the sensor. Applicants discovered that non-polar molecules with a high Henry's Law constant, such as acyclic hydrocarbons, will produce nucleated bubbles even when the analyte is in relatively low concentrations.

A second observed class did not produce the nucleated bubbles. However, a smaller, but measurable, decrease in a capacitance was still observed with increasing analyte concentration. Analytes that did not produce nucleated bubbles, are in a class of non-polar molecules having low Henry's Law constant, such as cyclic hydrocarbons. The measurable decrease in capacitance is believed due to physical displacement of higher dielectric water molecules from the sensor's electric field.

The present invention also teaches a differential sensor embodiment comprising an affinity sensor, as described above, with a reference capacitor sensor. The accuracy of the present invention is increased if differential sensing is employed. The reference capacitor compensates for changes in the dielectric constant of the liquid medium caused by changes in temperature, ionic concentration and the physical and chemical state of the liquid medium.

A first novel feature of the present invention is a sensor capable of detecting trace amounts of hydrocarbons, or other selected analytes, in a liquid medium.

A second novel feature is the use of a concentrating and nucleating layer to coat an "open" or planar capacitor, thereby causing the formation of nucleated bubbles in the fluid medium adjacent to that layer. The nucleated bubbles cause a dramatic decrease in capacitance with increasing analyte concentration.

A third novel feature is a sensor that provides an extremely sensitive response to solutions containing analytes that have non-polar molecules with high Henry's Law constant, such as acyclic hydrocarbons.

A fourth novel feature is a concentrating and nucleating layer made from selected polymeric materials having a high affinity to non-polar molecules (such as silicone rubber), and lipid materials.

A fifth novel feature is to detect an analyte in a liquid medium using a mechanism that displaces water molecules from the sensor's electrical field in proportion to analyte concentration.

A sixth novel feature is the use of a differential sensor having an analyte affinity sensor and a reference capacitor sensor. The reference capacitor sensor compensates for changes in the dielectric constant of the liquid medium caused by changes in ionic concentration and other physical or chemical states of the liquid medium.

A seventh novel feature involves presoaking the sensor with a salt matrix solution similar to that anticipated in the environment, to speed equilibration.

DETAILED DESCRIPTION OF THE EMBODIMENTS

Figure 1:
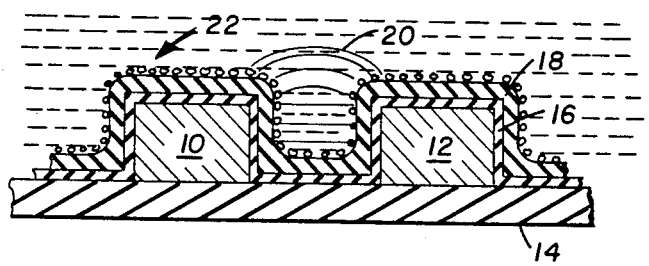
FIG. 1 is a schematic cross-sectional view of the invented capacitive sensor for detecting hydrocarbons, and other selected analytes, in a liquid medium.

FIG. 1 is a schematic cross-sectional view showing the general configuration of the capacitive chemical sensor. A first conductor 10 and a second conductor 12 are positioned on the surface of an insulating material or substrate 14. A first layer containing an electrically insulating material 16 coats the two electrodes. A active layer 18 also coats the two electrodes and may partially fill the channel formed between the two electrodes. The material for the active layer 18 is selected to have a relatively high affinity for non-polar molecules. As will be described later in the specification, various polymeric coatings such as silicone rubber have a high affinity for non-polar hydrocarbon molecules. When an alternating voltage is applied across the conductors, an electric field is generated having electrical lines of flux 20.

The resulting structure forms an "open" or planar capacitor that is directly exposed to a liquid medium containing selected non-polar analyte molecules in solution. When the capacitive sensor is exposed to such a liquid medium the capacitance of the sensor decreases as the concentration of the analyte molecules increases. The graph of FIG. 2 outlines experimental results using the invented sensor. The graph shows the inverse relationship between the measured capacitance of the sensor with increasing concentration of the hydrocarbon analyte in a fluid medium. The following experimental procedure was used to obtain these results.

1. A planar capacitive sensor was fabricated by depositing copper electrodes on a substrate forming an interdigitated pattern (see FIG. 3). The electrodes were approximately 2 mil wide, 1 mil high and separated by 3 mil spaces. The electrodes were coated with a thin electrically insulating layer using known deposition techniques to form the first layer (see FIG. 1, element 16). This insulating layer contained a 1 to 2.5 micron coating of parylene polymer deposited using known deposition processes and a 0.3 micron of SiO deposited using vapor vacuum evaporation deposition.

2. The planar capacitive sensor was then dipped in a 1% solution of RTV-118 silicone rubber in acetone to form the second layer 18 (see FIG. 1). The coating was then allowed to dry in air. The sensor was then immersed in distilled water and allowed to equilibrate over a period of hours.

3. After the sensor had equilibrated, its response to hydrocarbons was tested by adding molecules of a hydrocarbon into the distilled water surrounding the sensor. To speed solubility of the hydrocarbons, a 1% solution of a particular hydrocarbon in isopropyl alcohol was first made and this solution was added to the distilled water surrounding the sensor. (Previous experimentation showed no response of the sensor to alcohol in this concentration range.) The experiment was run for the following hydrocarbons with the sensor cleaned and allowed to equilibrate with fresh distilled water for each hydrocarbon; cyclohexane, benzene, pentane, hexane, and heptane.

4. The capacitance of the sensor was measured at 1 Khz with a GenRad 1657 RLC Digibridge. For each hydrocarbon tested, the capacitance of the sensor was measured as the concentration of the hydrocarbon in solution was increased. The graph of FIG. 2, shows the experimental results obtained.

Figure 2:
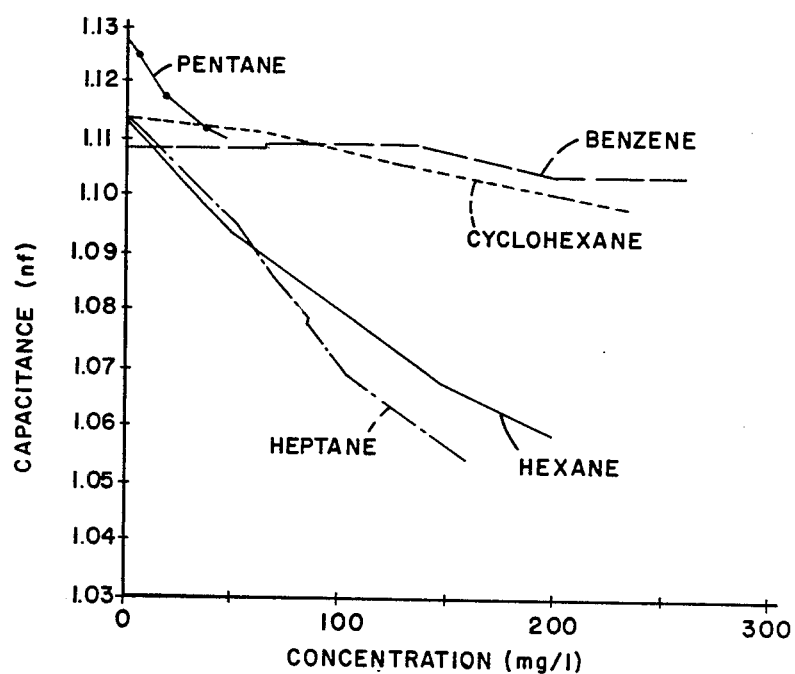
FIG. 2 is a graph showing the change in capacitance of the sensor for increasing concentration of various hydrocarbon analytes.

The graph of FIG. 2 demonstrates that the capacitance of the sensor decreases with increasing concentration of the following hydrocarbons: cyclohexane, benzene, pentane, hexane and heptane. However, with pentane, hexane and heptane, the capacitance decreased more drastically than with cyclohexane and benzene. Applicants observed that for the pentane, hexane, and heptane measurements nucleated bubbles formed in the liquid environment adjacent to the silicone rubber layer. Referring to FIG. 1, the nucleated bubbles 22 formed external to the silicone rubber layer 18. Applicants observed that the bubble formation was proportional to hydrocarbon concentration.

Applicants also observed that when the nucleated bubbles were removed by vibration or physical scrapping, they returned rapidly and the measured capacitance returned to the expected value.

Applicants believe that two classes of mechanisms account for these unexpected results. In both mechanisms the non-polar hydrocarbon molecules will preferentially enter the silicone rubber layer than be in the aqueous solution because of the high affinity of silicone rubber for non-polar molecules. The actual energy for this process comes from the attempt by water molecules to lower their potential energy by expelling the hydrocarbon molecules that separate the polar water molecules. Thus, the silicone rubber layer acts to absorb and concentrate hydrocarbon molecules from the solution. The first mechanism (which appears to dominate with acyclic hydrocarbons such as pentane, hexane and heptane) produces nucleated bubbles on the surface of the silicone rubber layer. The formation of nucleated bubbles on the surface of the silicone rubber layer produces high sensitivity of the sensor to these particular hydrocarbon molecules. The degree of bubble formation (as measured by the change in capacitance) increases as the total amount of hydrocarbon molecules in the liquid increase. It is estimated that the dielectric constant of the aqueous solution is approximately 78 or greater, and the dielectric constant of the bubbles is approximately 1-3. Therefore, formation of the bubbles displaces aqueous solution, and lowers the dielectric constant in the electric field of the capacitor (see generally, element 20, FIG. 1). Lowering the dielectric constant in the area of electric field causes a decrease in capacitance.

However, when the cyclic hydrocarbons were tested (such as cyclohexane and benzene) the generation of nucleated bubbles was not observed and the decrease in capacitance was less dynamic. Applicants believe the following theory may explain why the nucleation of bubbles occurs only with certain analytes. Silicone rubber concentrates hydrocarbons, or other non-polar analytes, from water because silicone rubber more readily dissolves the non-polar hydrocarbon molecules than the polar water molecules. This is an example of a hydrophobic effect. A hydrophobic effect is a manifestation of the desire of water molecules to orient in such a fashion as to maximize the hydrogen bonding among themselves. Non-polar compounds interfere with this bonding. The lowest energy way to accommodate the presence of the non-polar molecules is to concentrate them in as small a volume as possible. Hence the hydrocarbon molecules are "squeezed" into the silicone rubber. This process results in high concentration of hydrocarbon molecules in the vicinity of the silicone rubber/water interface. When the amount of hydrocarbon squeezed into this space exceeds the solubility of the material in water, a phase transition can take place and a bubble can be formed. The presence of irregularities in the silicone rubber layer probably help to nucleate the formation of the bubbles. The presence and degree of bubble formation can be related to Henry's Law constant for the particular hydrocarbon or other analyte material. Henry's Law (P=kC) states that the partial pressure (P) of a volatile solute above a solution of that solute in a solvent is proportional to the concentration (C) of that solute in the solution. The Henry's Law constant is thus a measure of how poorly the solute is tolerated by the solvent. An article written by Douglas MacKay and Wan Ying Shiu entitled "Critical Review of Henry's Law Constants for Chemicals of Environmental Interest", *J.Phys.Chem.Ref.Data*, Vol. 10, No. 4, pages 1175-1199, 1981, gives Henry's Law constants (k) and the solubility of various materials in solution. Table I summarizes the Henry's Law constants (k) and solubility for the hydrocarbon materials tested above. The hydrocarbon materials that show nucleated bubble formation are shown by an (*) in Table I. It is apparent that the bubble formers have a higher Henry's Law constant and a lower solubility than the low bubble formers. This explains why nucleation of bubbles occurs with pentane, hexane and heptane, but not with cyclohexane and benzene, as shown in FIG. 2.

TABLE I

HENRY'S LAW CONSTANTS, SOLUBILITIES AND VAPOR PRESSURES FOR SEVERAL HYDROCARBONS AT 25 DEGREES C.

| Substance | Henry's Law Constant (kPa cubic m/mole) (2) | Solubility (g/cubic m) | Vapor Pres. (kPa) |
|---|---|---|---|
| n-Pentane* | 125 | 41.2 | 68.4 |
| n-Hexane* | 170 | 12.5 | 20.2 |
| Cyclohexane | 18.0 | 59.7 | 12.7 |
| n-Heptane* | 230 | 2.68 | 6.11 |
| Benzene | 0.550 | 1437 | 12.7 |
| Toluene | 0.670 | 1391 | 3.80 |

The theory must also explain why bubbles remain in the vapor state. To prevent collapse, the total pressure in the bubble must be approximately one atmosphere. It is believed that the one atmosphere of pressure is essentially contributed by hydrocarbon vapor, although water vapor and constituents of air may provide a portion of the necessary pressure to maintain the bubble. Henry's Law indicates that the necessary vapor pressure can be achieved with low concentration levels of the hydrocarbon analytes that have large Henry's Law constants. This is due to the concentrating effect of the silicone rubber layer. Applicants believe that in certain situations the nucleated bubbles may actually be super-/saturated vapor and exist at higher vapor pressures than indicated in Table I.

The above mechanism indicates that nucleated bubbles are expected for hydrocarbon analytes having relatively large Henry's Law constant. Summarizing the results in Table I, we can see that hydrocarbons that produce nucleated bubbles (such as pentane, hexane and heptane) had Henry's Laws constant that ranged from 125-230; however, hydrocarbons that did not exhibit bubble formation or exhibited low bubble formation, such as cyclohexane and benzene, had Henry's Law constants ranging from 0.5 to 18. This highly sensitive bubble formation mechanism enables the invented sensor to detect non-polar molecules having relatively large Henry's Law constants.

Although bubble formation was not observed with cyclohexane and benzene, Applicants believe a second mechanism may account for the observed decreases in capacitance with increasing hydrocarbon concentration. This second mechanism also occurs because higher dielectric water molecules are displaced from the area of the electric field. Once hydrocarbon molecules are absorbed into the silicone rubber layer, the following may occur: (1) they displace water molecules in the silicone rubber layer thus lowering the overall dielectric constant (Note: the dielectric constant of water is approximately 78, or greater, and the dielectric constant of hydrocarbons is approximately 1-3); (2) the silicone rubber swells when it absorbs hydrocarbons this swelling pushes the higher dielectric water molecules away from the area of the electric field. Since the lower dielectric silicone rubber has swelled (dielectric constant approximately 3) and displaced the higher dielectric water (dielectric constant approximately 78, or greater) a small decrease in the capacitance will be observed. Applicants believe that the water displacement mechanisms may occur simultaneously with the bubble formation mechanism discussed earlier; although, the bubble formation mechanism produces the most dramatic and sensitive response.

Applicants believe that the results they obtained in FIG. 2, were unexpected in light of the prior art. The nucleation of bubbles on the sensor surface was not expected. Nor was a decrease in the capacitance with increasing hydrocarbon concentration due to the displacement of water molecules expected. A prior art reference, previously cited (U.S. Pat. No. 4,453,126), uses a planar capacitor with a silicone rubber dielectric to detect anesthetic gas such as halothane and enflurane in a gas mixture. That cited reference teaches an increase in capacitance with an increase in concentration of the anesthetic. Applicants with their invented sensor have observed the opposite effect, that is, the measured capacitance decreases with increasing hydrocarbon concentration. This result, as well as the formation of bubbles on the sensor surface, is unexpected in light of this reference.

Figure 3:
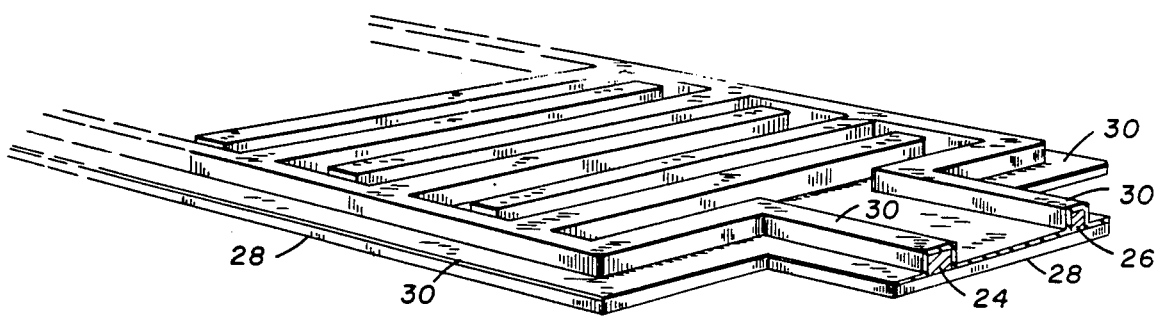
FIG. 3 is a perspective view of an "open" capacitor that uses a plurality of interdigitated fingers.

FIG. 3 is a perspective view of a planar capacitor having a plurality of interdigitated fingers. Metallic electrodes or conductors 24 and 26 are positioned on an insulating substrate 28. Each electrode has a plurality of fingers that are disposed in an interdigitated manner relative to the fingers of the other electrodes. The interdigitated fingers from both electrodes form a plurality of channels. Known photolithographic etching techniques are used to form the interdigitated fingers on a substrate. The substrate can be made from insulating material such as Corning 7059 glass or alumina wafers. The interdigitated fingers can be made of copper and/or gold. Applicants selected 2 mil wide fingers that are approximately 1 mil high and separated by 3 mil spaces, although other dimensions may be used. The interdigitated fingers are covered with an insulating layer 30. Applicants made the insulating layer 30 with a 1-2.5 micron coating of parylene polymer deposited using known deposition processes and a 0.3 micron of SiO deposited using vapor vacuum evaporation deposition; however, alternative electrical insulating material can be used. To complete the sensor, a second layer of a material that has a high affinity for non-polymer molecules coats the insulating layer 30. (The second, or active layer 18 is best shown in FIG. 1.) As discussed earlier, this second layer can be made from various polymeric materials such as silicone rubber, as well as the following non-limiting materials: polyurethane, ethylene propylene rubber, styrene butadiene, polyacrylate, iso-butylene isoprene and various lipid materials. Liquid to be tested for a particular analyte is brought into contact with the planar capacitor as discussed earlier. It is to be understood that other geometries of the planar capacitor can provide the desired feature of the open capacitor. For example, the electrode elements of the capacitor can be interleaved on the substrate or, parallel electrode elements can be embedded in a molded insulator with the active layer coating the molded insulator. Further, the electrode elements 24 and 26 of the capacitor can be made from doped semiconductor materials, such as doped silicon.

It is also to be understood that, although the sensor was described detecting hydrocarbons, other analytes can be detected. For instance, the bubble mechanism would detect most non-polar molecules having a relatively large Henry's Law constant. Further, although the liquid medium has been described in terms of distilled water, any aqueous solution would work. Applicants ran tests with sodium chloride aqueous solutions and found satisfactory detection of the hydrocarbon analytes. It is also to be understood that the liquid medium may be non-aqueous liquids.

Figure 4:
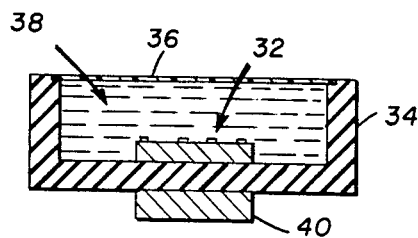
FIG. 4 is a schematic cross-sectional view of the analyte sensor positioned in a protective casing.

FIG. 4 is a schematic representation of the sensor that is packaged for use as an environmental sensor. The planar capacitor 32 (designed in accordance with this specification) is securely fixed in a casing 34. A membrane 36 allows solutions to enter the interior of the casing from the environment and to contact the sensor 32. The membrane 36 protects the sensor from abrasive particles in the environment. A polycarbonate sheet with about 0.2 micron etched pores is suggested for the membrane. In one embodiment, the sensor and casing can be presoaked in a salt matrix solution 38 similar to solutions found in the test environment. Such presoaking would be advantageous to reduce the time to equilibrate to new salt concentrations. In another embodiment, where continuous analyte concentrations measurements must be made, a vibrator 40, such as piezoelectric oscillator is used to periodically shake nucleated bubbles from the sensor. This feature would increase the dynamic response of the sensor and allow continuous or time trend measurements.

Figure 5:
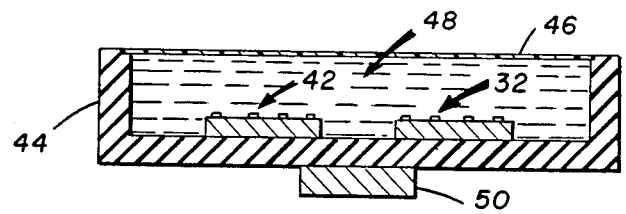
FIG. 5 is a schematic cross-sectional view of a differential capacitive sensor comprising an analyte capacitor sensor and a reference capacitor sensor.

FIG. 5 is a schematic representation of a differential sensor embodiment that includes both the analyte sensor 32 and a reference capacitor 42. The accuracy of the present invention is increased if differential sensing is used. The reference capacitor 42 compensates for changes in the dielectric constant of the liquid medium caused by changes in temperature, ionic concentration, pH, composition and the physical and chemical state of a liquid medium. The reference capacitor 42 is identical in design to the sensor capacitor, except the second or concentrating layer is not used. Therefore, the reference capacitor comprises two electrodes positioned on a substrate coated with an insulating layer to form a capacitor. In the embodiment shown in FIG. 5, the analyte sensor 32 and the reference capacitor sensor 42 are mounted within casing 44. A membrane 46 allows solutions to enter the interior of the casing from the environment and to contact both analyte sensor 32 and the reference capacitor sensor 42. The membrane 46 protects the sensor from abrasive particles in the environment and can be made from a polycarbonate sheet with 0.2 micron etched pores. The analyte sensor and casing can be presoaked in a salt matrix solution 48, similar to the solutions found in the test environment. As discussed previously, such presoaking enables the sensor to be sold in a state equilibrated to expected environmental salt concentrations. Also, as discussed previously, a vibrator 50 such as a piezoelectric oscillator, can be used periodically to shake nucleated bubbles free from the analyte sensor. This allows the sensor to make accurate continuous or time trend measurements.

Figure 6:
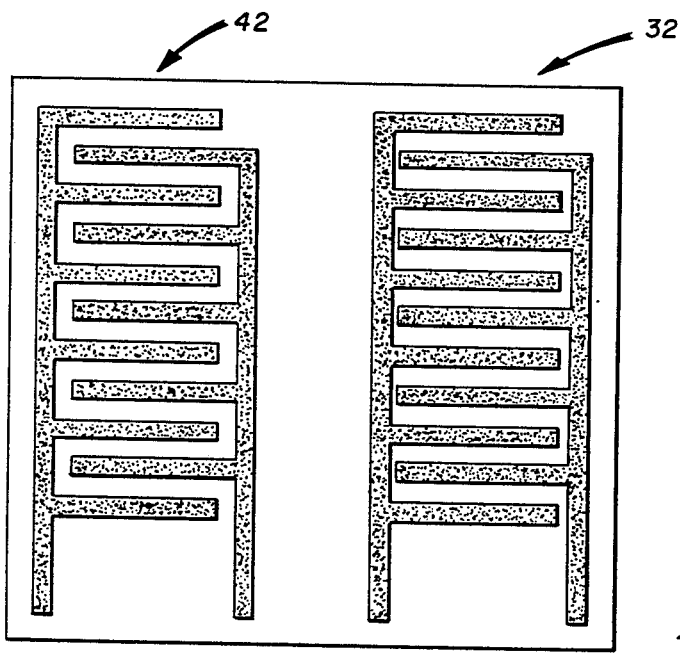
FIG. 6 is an embodiment of the differential capacitive sensor having the affinity capacitor and the reference capacitor located side by side.
Figure 7:
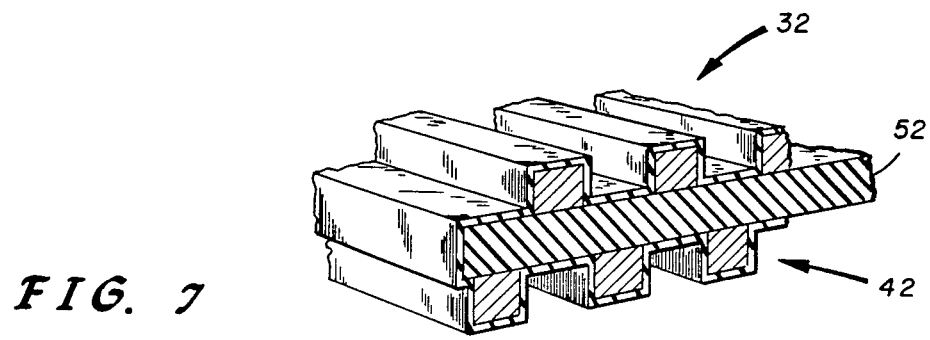
FIG. 7 is an embodiment of the differential capacitive sensor having the affinity capacitor and the reference capacitor located back to back.

FIGS. 6 and 7 various embodiments for a differential sensor that includes an analyte sensor 32 and reference capacitor sensor 42. FIG. 6 is a top view of the analyte sensor 32 and reference capacitor 42 located side by side on the same substrate. FIG. 7 is a cross-sectional view of the analyte sensor 32 and reference capacitor 42 located back to back. A shield 52 located between the capacitors can be used to isolate the electric field generated by each capacitor. With both the side by side and back to back embodiments, the fluid medium under test would be simultaneously introduced onto both the sensor capacitor and reference capacitor. For simplicity of illustration, the analyte sensor shown in FIGS. 7 and 8 do not show the second layer of polymeric material which covers the insulating layers.

Figure 8:
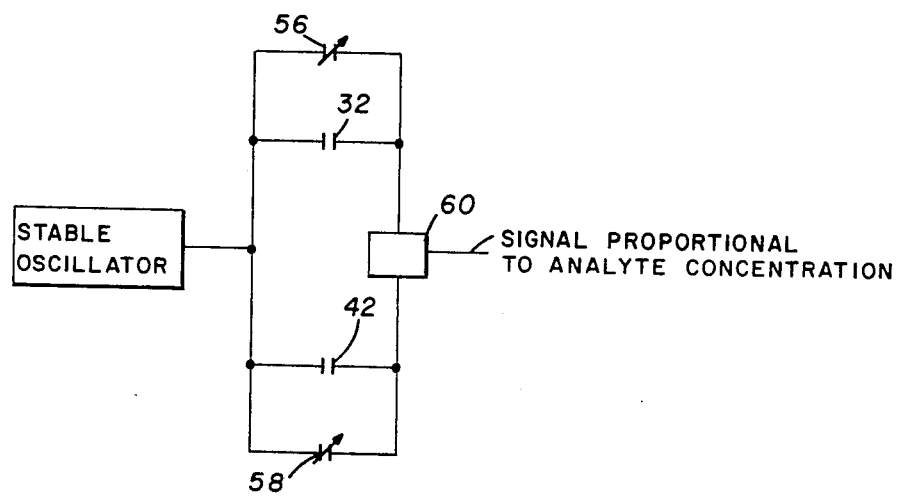
FIG. 8 is a schematic diagram of a circuit to detect the phase difference between the affinity capacitor and the reference capacitor.
Figure 9:
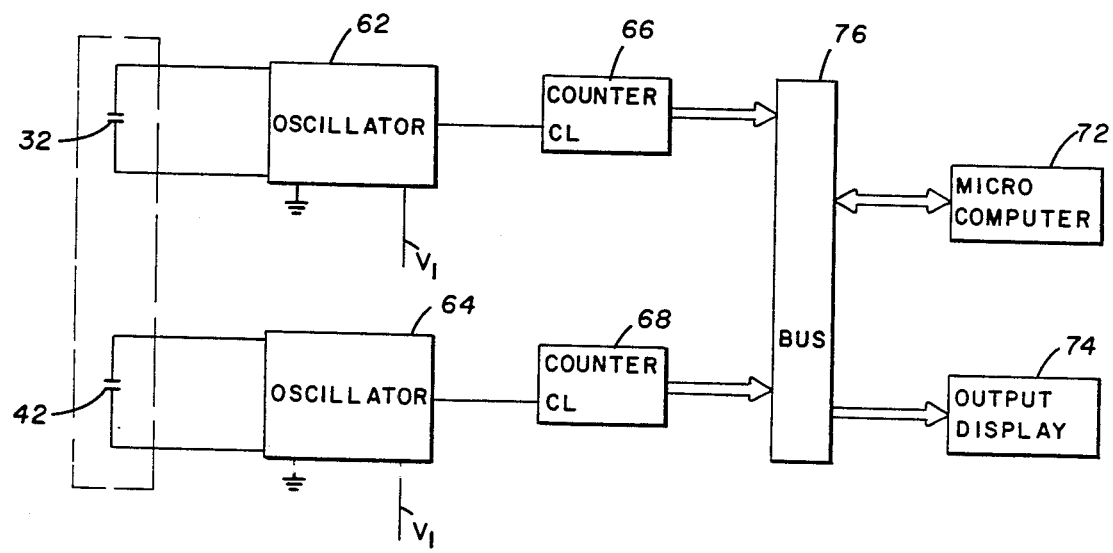
FIG. 9 is a schematic diagram of a microprocessor system for use with a differential affinity sensor that has an affinity capacitor and a reference capacitor.

FIGS. 8 and 9 are schematic diagrams which illustrate two possible circuits to be used with a differential sensors as taught by the present invention. FIG. 8 is a schematic diagram of the circuit to detect the phase difference between the analyte sensor 32 and reference capacitor 42. The stable oscillator 54 supplies an alternating signal to the analyte capacitor 32 and the reference capacitor 42. These capacitors are placed in parallel with trim capacitors 56 and 58. Phase detector 60 detects the phase angle shift between the analyte capacitor 32 and the reference capacitor 42. The phase shift is functionally related to the analyte concentration in the fluid medium.

FIG. 9 is a schematic diagram of a microprocessor system for use with a differential sensor. The system contains an analyte capacitor 32 and reference capacitor 42. The analyte and reference capacitors (32, 42) are brought into contact with the liquid medium under test. Each capacitor is connected to an oscillator (62, 64) and a change in the capacitance will alter the frequency of oscillation of its associated oscillator. The output frequency of each oscillator (62, 64) is fed to an associated counter (66, 68) which sends the frequency count in digital form via bus 70 to microprocessor 72. A look-up table containing data similar to that shown in FIG. 2, is stored in the microcomputer and a determination of the concentration of the analyte in the fluid medium is made. This value is displayed on output display 74. It is to be understood that other circuits can also be envisioned once one understands the differential change in capacitance between the analyte capacitor and the reference capacitor as taught by the present invention.

The capacitive chemical sensor may be integrated with measurement and signal processing electronics to form either a monolithic integrated circuit chip or hybrid circuit. For example, the capacitive chemical sensor could be integrated in the gate circuit of a field effect transistor (ET) to yield a "floating gate" FET configuration.

Obviously many modifications and variations of the present invention are possible in light of the above teachings. It is therefore to be understood that within the scope of the appended claims, the invention may be practiced otherwise than is specifically described.

What is claimed is:

1. A device for sensing selected analyte in a liquid medium, comprising:
   a concentrating and nucleating material adapted to be exposed to a liquid medium under test, for causing nucleated formation of bubbles in a liquid medium on the surface of said material in response to selected analyte contained in said liquid medium; and,
   a means, positioned in association with said concentrating and nucleating material, responsive to the formation of said bubbles.

2. The device of claim 1, wherein said responsive means is a capacitor and wherein said bubble formation causes a change in capacitance with increasing analyte concentration.

3. The device of claim 1, wherein said responsive means is a capacitor having at least one pair of spaced apart electrode elements, and wherein said bubble formation causes a decrease in capacitance with increasing analyte concentration.

4. The device of claim 1, wherein said concentrating and nucleating material is a material having an affinity to non-polar molecules, wherein non-polar analyte molecules having a high Henry's Law constant tend to nucleate in the liquid medium on the surface of said material.

5. The device of claim 1, wherein said concentrating and nucleating material is selected from the group consisting of polymeric and lipid materials having a high affinity to non-polar molecules.

6. The device of claim 1, wherein said concentrating and nucleating material is selected from a group consisting of: polyurethane, ethylene propylene rubber, styrene butadiene, polyacrylate, silicone rubber, and isobutylene isoprene.

7. The device of claim 1, wherein said concentrating and nucleating material is silicone rubber.

8. The device of claim 3, wherein said electrode elements are made from doped semiconductor material.

9. The device of claim 3, wherein said electrode elements are made from electrically conductive material.

10. The device of claim 3, further comprising an electronic means, operably coupled to said capacitor, for measuring and displaying the change in capacitance.

11. A device for sensing a selected analyte in a liquid medium, comprising:
    a capacitor having at least one pair of spaced apart electrode elements; and,
    a concentrating and nucleating material positioned in association with said electrode elements and adapted to be exposed to liquid medium under test, for causing nucleated formation of bubbles in a liquid medium on the surface of said concentrating and nucleating material, thereby decreasing capacitance with increasing analyte concentration.

12. The device of claim 11, wherein an electrically insulating material separates said at least one pair of electrode elements from said concentrating and nucleating material.

13. The device of claim 12, wherein said electrically insulating material forms a first layer coating at least a portion of said electrode elements and wherein said concentrating and nucleating material forms a second layer coating at least a portion of said first layer.

14. The device of claim 13, wherein said at least one pair of spaced apart electrical elements form a channel therebetween, and wherein said concentrating and nucleating material fills at least a portion of said channel.

15. The device of claim 11, wherein said concentrating and nucleating material is a material having an affinity to non-polar molecules, wherein non-polar analyte molecules having a high Henry's Law constant tended to nucleate in the liquid material on the surface of said material.

16. The device of claim 11, wherein said concentrating and nucleating material is selected from the group consisting of polymeric and lipid materials having a high affinity to non-polar molecules.

17. The device of claim 11, wherein said concentrating and nucleating material is selected from a group consisting of: polyurethane, ethylene propylene rubbe, styrene butadiene, polyacrylate, silicone rubber, and iso-butylene isoprene.

18. The device of claim 11, wherein said concentrating and nucleating material is silicone rubber.

19. The device of claim 11, wherein said electrode elements are made from doped semiconductor material.

20. The device of claim 11, wherein said electron elements are made from a electrically conductive material.

21. The device of claim 11, further comprising an electronic means operably coupled to said capacitor, for measuring and displaying the change in capacitance.

22. A device for sensing a hydrocarbon analyte in an aqueous selection, comprising:
a capacitor having at least one pair of spaced apart electrode elements; and,
a layer of polymeric material positioned in association with said electrode elements and adapted to be exposed to an aqueous solution under test, for causing nucleated formation of bubbles in the aqueous solution on the surface of said layer in response to presence of hydrocarbon analytes in said aqueous solution, thereby decreasing capacitance with increasing concentration of said hydrocarbon analyte.

23. The device of claim 22, wherein said polymeric material is a material having a high affinity to hydrocarbon molecules.

24. The device of claim 23, wherein said polymeric material is a selected from a group consisting of: polyurethane, ethylene propylene rubber, styrene butadiene, polyacrylate, silicone rubber, iso-butylene isoprene.

25. The device of claim 23, wherein said polymeric material is silicone rubber.

26. The device of claim 22, wherein said electrode elements are made from doped semiconductor material.

27. The device of claim 22, wherein said electron elements are made from electrically conductive material.

28. The device of claim 22, further comprising an electronic means operably coupled to said capacitor, for measuring and displaying the change in capacitance.

29. The device of claim 22, further comprising a means for periodically vibrating said polymeric layer thereby removing bubbles from the surface of said polymeric layer, so as to allow the sensor to make continuous hydrocarbon concentration measurements.

30. The device of claim 22, wherein said capacitor is positioned in a protective casing, and wherein a portion of said casing contains a porous membrane allowing liquid to penetrate said casing.

31. A differential sensor for sensing hydrocarbon analyte in a liquid medium comprising:
a first capacitor having at least one pair of spaced apart electrode elements;
a layer of polymeric material positioned in association with said electrode elements of said first capacitor and adapted to be exposed to a liquid medium under test, for causing nucleated formation of bubbles in the liquid medium on a surface of said layer in response to analyte hydrocarbon contained in the liquid medium;
a second capacitor having at least one pair of spaced apart electrode elements;
a layer of electrically insulating material coating said spaced apart electrode elements of said second capacitor and adapted to the exposed to said liquid medium under test; and,
an electronic means, operably connected to said first and second capacitor for calculating the hydrocarbon concentration in said liquid medium.

32. The device of claim 31, wherein said polymeric material is selected from a group consisting of: polyurethane, ethylene propylene rubber, styrene butadiene, polyacrylate, silicone rubber iso-butylene isoprene.

33. The device of claim 31, wherein said polymeric material is silicone rubber.

34. The device of claim 31, wherein an electrically insulating material separates said at least one pair of electrode elements of said first capacitor, from said polymeric layer.

35. The device of claim 31, further comprising a means for periodically vibrating said polymeric layer thereby removing bubbles from the surface of said polymeric layer so as to allow the sensor to make continuous analyte concentration measurements.

36. The device of claim 31, wherein said first and second capacitor are positioned in a protective casing, and wherein a portion of said casing contains a porous membrane allowing liquid to penetrate such casing.

37. A device for sensing a hydrocarbon analyte in a liquid medium comprising:
a substrate;
a plurality of spaced apart finger electrodes positioned on said substrate to form an open sensor capacitor;
a first electrically insulating layer coating said finger electrodes of said sensor capacitor; and,
a second layer of polymeric material coating said first layer and at least partially filling a volume between said spaced apart finger electrodes and adapted to be exposed to the liquid medium under test, wherein said polymeric material has an affinity for non-polar hydrocarbon molecules, thereby causing a decrease in capacitance of said sensor capacitor with increasing hydrocarbon concentration.

38. The apparatus of claim 37, wherein said second layer is selected from the group consisting of: polyurethane, ethylene propylene rubber, styrene butadiene, polyacrylate, silicone rubber and iso-butylene isoprene.

39. The device of claim 37, wherein said second layer is made from silicone rubber.

40. The device of claim 37, wherein said capacitor is positioned in a protective casing, and wherein the portion of said casing contains a porous membrane allowing liquid to penetrate said casing.

41. The device of claim 37, further comprising a liquid medium containing a selected salt concentration that fills at least a portion of said casing.

42. The device of claim 37, further comprising a means for periodically vibrating said second layer thereby removing bubbles from the surface of said second layer, so as to allow the device to make continuous analyte concentration measurements.

43. The device of claim 37, further comprising a reference capacitor having: a substrate; a plurality of spaced apart finger electrodes positioned on said substrate to form an open capacitor; and, an electrically insulating layer coating said finger electrodes, and adapted to be exposed to the fluid medium under test.

44. The device of claim 43, further comprising an electronic means, operably connected to said sensor capacitor and said reference capacitor, for calculating the hydrocarbon concentration in the liquid medium under test.

45. The device of claim 44, wherein said sensor capacitor, said reference capacitor, and said electronic means, are integrated onto a single integrated circuit chip.

* * * * *

UNITED STATES PATENT AND TRADEMARK OFFICE
CERTIFICATE OF CORRECTION

PATENT NO. : 4,728,882

DATED : March 1, 1988

INVENTOR(S) : William D. Stanbro and Arnold L. Newman

It is certified that error appears in the above—identified patent and that said Letters Patent is hereby corrected as shown below:

In the claims:

Column 10, line 57, delete "the" and insert therefor -- a --

Column 11, line 17, delete "rubbe" and insert therefor -- rubber --

Column 12, lines 53-54, after "thereby causing" and before "a decrease" insert -- formation of nucleated bubbles of hydrocarbon which causes --

Column 13, line 4, delete "surfacc" and insert therefor -- surface --

Signed and Sealed this

Sixteenth Day of August, 1988

Attest:

DONALD J. QUIGG

Attesting Officer     Commissioner of Patents and Trademarks